(12) United States Patent
Jensen et al.

(10) Patent No.: US 10,612,851 B2
(45) Date of Patent: Apr. 7, 2020

(54) EARLY DETECTION OF SMOLDERING POWDERS IN POWDER DRYING SYSTEMS COMPRISING A CO GAS DETECTION SYSTEM

(71) Applicant: GEA Process Engineering A/S, Søborg (DK)

(72) Inventors: Poul Erik Krogsgaard Jensen, Greve (DK); Gerhardt Jacobsen, Værløse (DK); Anders Sehested, Roskilde (DK)

(73) Assignee: GEA Process Engineering A/S (DK)

( * ) Notice: Subject to any disclaimer, the term of this patent is extended or adjusted under 35 U.S.C. 154(b) by 0 days.

(21) Appl. No.: 16/484,915

(22) PCT Filed: Feb. 9, 2017

(86) PCT No.: PCT/DK2017/050033
§ 371 (c)(1),
(2) Date: Aug. 9, 2019

(87) PCT Pub. No.: WO2018/145706
PCT Pub. Date: Aug. 16, 2018

(65) Prior Publication Data
US 2019/0383557 A1    Dec. 19, 2019

(51) Int. Cl.
*G08B 17/10*    (2006.01)
*F26B 25/00*    (2006.01)
(Continued)

(52) U.S. Cl.
CPC .......... *F26B 25/009* (2013.01); *F26B 25/007* (2013.01); *G01N 21/3504* (2013.01);
(Continued)

(58) Field of Classification Search
CPC .. F26B 3/06; F26B 3/12; F26B 25/007; F26B 25/009; F26B 11/12; G01N 21/3504; G01N 21/85; G01N 33/004
(Continued)

(56) References Cited

U.S. PATENT DOCUMENTS

| | | | |
|---|---|---|---|
| 2012/0047995 A1* | 3/2012 | Fleischer | G08B 17/117 73/29.02 |
| 2016/0054059 A1 | 2/2016 | Forsyth et al. | |
| 2017/0082573 A1* | 3/2017 | Vingerhoets | G01N 27/416 |

FOREIGN PATENT DOCUMENTS

| | | |
|---|---|---|
| DE | 202014101777 U1 | 6/2014 |
| GB | 2218192 A | 11/1989 |

(Continued)

*Primary Examiner* — Toan N Pham
(74) *Attorney, Agent, or Firm* — Condo Roccia Koptiw LLP (57) ABSTRACT

The invention concerns a powder drying system (1) comprising a carbon monoxide (CO) gas detection system adapted for detection of CO gas from smoldering powders in a powder drying system component, such as a spray dryer chamber (200), a fluid bed (500) or a bag filter (400), which CO gas detection system comprises at least one inlet CO gas detector (3) arranged on at least one gas inlet of a powder drying system component such as to provide at least one inlet CO gas content measurement, at least one outlet CO gas detector (3) arranged on at least one gas outlet of a powder drying system component such as to provide at least one outlet CO gas content measurement, and an analyzing unit (5) adapted for receiving the at least one inlet CO gas content measurement, receiving the at least one outlet CO gas content measurement and comparing the sum of the at least one inlet CO gas content measurement and the sum of the at least one outlet CO gas content measurement while compensating for dilution, mixing, and time delay of the outlet CO gas content measurement. At least the at least one
(Continued)

outlet CO gas detector (3) comprises an IR laser transmitter and is adapted for detecting over a measurement volume (6) and is arranged on the at least one gas outlet in such a way that said measurement volume (6) extends directly inside a gas flow (20) in said at least one gas outlet.

10 Claims, 4 Drawing Sheets

(51) Int. Cl.
*G01N 21/3504* (2014.01)
*G01N 33/00* (2006.01)
*G01N 21/85* (2006.01)
*F26B 3/12* (2006.01)

(52) U.S. Cl.
CPC ........... *G01N 21/85* (2013.01); *G01N 33/004* (2013.01); *F26B 3/12* (2013.01); *G01N 2021/8578* (2013.01)

(58) Field of Classification Search
USPC ........................................................ 340/632
See application file for complete search history.

(56) References Cited

FOREIGN PATENT DOCUMENTS

| | | |
|---|---|---|
| WO | 2016-116024 A1 | 7/2016 |
| WO | 2017-048752 A1 | 3/2017 |

\* cited by examiner

EARLY DETECTION OF SMOLDERING POWDERS IN POWDER DRYING SYSTEMS COMPRISING A CO GAS DETECTION SYSTEM

CROSS REFERENCE TO RELATED APPLICATIONS

This application is the National Stage Entry under 35 U.S.C. § 371 of Patent Cooperation Treaty Application No. PCT/DK2017/050033, filed 9 Feb. 2017, the contents of which are hereby incorporated by reference herein.

FIELD OF INVENTION

The present invention relates to a powder drying system with a system adapted for early detection of smoldering powders in a powder drying system component, such as a spray dryer chamber, a fluid bed or a bag filter, by detecting the carbon monoxide (CO) gas emitted during smoldering.

Note that the term "measurement volume" as used herein is intended to refer to the volume, area, line, and/or point from which the CO gas detection system receives measurement information is arranged, or in other words is covered by a measurement performed by the CO gas detection system.

Note that the term "measurement range" as used herein is intended to refer to the position in which the measurement volume is to be arranged, and may thus encompass not only the actual measurement volume but also a zone or buffer zone immediately adjacent to the measurement volume.

Note that the term "gas" as used herein is to be interpreted as encompassing any gas that is suitable as process gas in such a spray drying system. Some non-limiting examples of gasses are process gasses, such as atmospheric air and suitable oxygen- or nitrogen-enhanced gases.

Note that the term "powder drying system" is intended to encompass such systems in which a powdery or particulate material is formed and/or processed. The material may either be provided as a feed of powdery or particulate material, or as a liquid feed to be dried. The powder drying system is also intended to cover cooling of the particulate material. In addition, or alternatively, to the spray dryer described, such a system could include one or more fluid beds, cyclones, bag filters, pneumatic transport systems, feed pretreatment etc. The powder drying system thus incorporates a unit for forming or processing powder in any suitable manner. Non-limiting examples encompass a spray dryer, fluid bed, flash dryer, ring dryer, spray dryer with integrated or external fluid bed, cyclone, etc. In general, a powder drying system has an inlet for a liquid, paste or solid feed e.g. at the top of a vertical dryer, where a liquid feed enters the dryer and meets a stream of dry, hot air so that droplets of feed will fall down inside the dryer and liquid will be removed from the droplets resulting in formation of substantially dry particles. The liquid feed may be a slurry or suspension of particles or a solution capable of forming particles upon removal of the solvent.

Note that the term "powder drying system component" is intended to encompass any component of a powder drying system in which a process gas is present at least during operation, such as but not limited to drying chambers, fluid beds, bag filters, cyclones, ducts, such as cleaning arrangements connecting ducts.

Note that the term IR laser transmitter is intended to encompass any laser light source, such as a laser setup or diode that can emit IR radiation in the IR wavelength band, defined by electromagnetic radiation with wavelengths in the range of around 700 nm to around 1 mm.

Note that the term IR receiver is intended to encompass any detector that can detect IR radiation.

BACKGROUND OF THE INVENTION

Smoldering powders, so-called nests, i.e. particulate burning embers and agglomerates, are common ignition sources in dust explosions and fires, and pose a serious threat in powder drying systems, such as spray dryers, that produce powders within food, pharmaceuticals, dairy, chemical, agrochemical, energy, biotechnology, healthcare and many more, producing e.g. milk powder, coffee whitener, infant formula, coffee powder, pharmaceutical, chemical, etc. During a spray drying process deposits may occur when generally not-high-temperature-droplets accumulate in smaller or larger deposits on walls or floors of driers. The product temperature of such deposits may rise due to intrinsic chemical reactions, which may cause the powder to smolder, or even burn when in oxygen filled atmospheres. During smoldering, CO gas production starts, and an oxidation and/or pyrolysis reaction occurs. Lumps of deposited smoldering product may typically develop inside the spray-chamber and/or air disperser/and/or atomizer, cyclone or in an interior or exterior fluid bed, or in exterior bag filters.

If powder deposits are not removed from the drying system and reach a certain size, they may form lumps and fall down inside the system, even travel through the process and break-up so a so-called glowing mass, initiated by heat as an exothermal oxidation reaction. The glowing mass may become exposed and ignite a powder filled atmosphere at some point in time. Another scenario is that larger lumps of powder are subjected to heat, e.g. at the bottom of a fluid-bed and smoldering reactions are activated. This can take place also in low oxygen atmospheres or the like. Subsequently, the smoldering lump may travel through the process and finally result in plant fires or dust explosions. Primary fire prevention is typically based on temperature surveillance and regular cleaning practices. Often, such primary prevention is not fast enough due to process reaction delay and therefore insufficient; and additional measures are implemented in the form of smoldering detection systems for early warning and protection of the drying system.

One prior art solution is produced and marketed by FIKE under the name WarnEx. This system consists of multiple so-called sampling and detection units (SDUs) placed on each inlet and outlet of a powder drying system and a control unit processing the signals received from the SDUs. The WarnEx system thus employs extraction of samples in the sampling part of an SDU and transport of the detection result to the detection part of the SDU through suitable electric cabling.

DE 202014101777 U1 describes a spray dryer with a humidity detector having a measuring device, which humidity detector may also be used for detection of CO gas. The specific type of measuring device and measuring method employed in detection of CO gas by means of the humidity detector is, however, not mentioned.

Furthermore, DE 202014101777 U1 and other known CO gas detection systems for spray dryers employ extraction of gas samples from the flow at least at an inlet and at an outlet thereof, and transport these gas samples via e.g. Teflon® tubes to a common IR laser or a common NDIR detector system (not laser) provided at a distance from the chamber. Such CO gas detection systems are produced and marketed by e.g. Hobré Instruments and ATEX CO.

However, the known CO gas detection systems have several disadvantages, including:
- reduced result reliability when measuring on a small volume of gas in a gas sample,
- the sample may not be representative for the actual CO gas concentration in the flow out or in as it depends on the airflow and dilution at the selected extraction position,
- they require accurate timing between the physical gas sample from the in/outlet in the system,
- need for frequent calibration to ensure the required sensitivity at all times, in particular when the flow rates or volume size of drier changes,
- high acquisition, installation, operation, maintenance and verification/calibration costs, and
- is difficult to adapt to changes in flow or volume size of dryer, and
- requires external control signals from another source.

Furthermore, the prior art systems, such as those of ATEX CO and Hobré, as mentioned employ tubing to transport the gas samples from the sampling site to the measurement site, i.e. the common external detector. Such tubing requires maintenance, may leak, is ergonomically difficult to handle when installing and requires a large detector system cabinet and high power consumption. Additionally, their system cabinet (of the floor standing type) requires certain conditions for the installation area, like the temperature shall be below 25° C., it has to be installed in a clean confined environment and access to the cabinet from several sides, and a water drain is necessary for drainage of condensate coming from the system. Also, humidity in the samples must be removed before measurement, and it is needed for the detector system calculation to be compensated for e.g. different geometries or flows inside the tubes, so that repairs on tubes and connectors cannot be performed by plant staff but must be undertaken by professionals, e.g. detector providers.

The response time of a CO gas detection system should be low and preferably real time and the sensitivity high in order to provide an effective early warning system.

However, the transport time of the air samples, added to the detector purge time, analysis time, calculation time and the intrinsic holding time in the common measurement chamber adds up to longer response times for these prior art systems of around 15-60 seconds. It is desirable to decrease this response time, which may prove too long to constitute early warning. As for sensitivity, some of the prior art systems are incapable of detecting CO gas concentrations of generally below about 1 ppm and for the best prior art systems below about 0.4 ppm. To provide for an effective early warning system it is, however, desired to provide a sensitivity enabling detection of CO gas concentrations generally being below 0.4 ppm and preferably below 0.1 ppm.

During initial commissioning of prior art CO gas detection systems for spray dryer systems, tests are needed where hazardous CO gas are injected into the entire dryer system for testing the gas retention time for necessary calibration procedure of the CO gas detection. Importantly, the purchase and handling of CO gas normally requires local regulatory approval. With some of the prior art systems as stipulated by the spray dryer systems risk assessment or to ensure optimal system performance require an enhanced test carried out frequently on the system before a spray dryer system is released for operation. One of the steps in this test is use of a special certified test gas consisting of $N_2$+CO (CO=8.0 ppm) to confirm that the CO gas detection is measuring correctly. The test gas is expensive and not commonly available on the market. Another requirement is leak tests of sample tubes for prior art CO gas detection systems. This test must frequently be carried out to ensure that the CO gas detection system actually is measuring the process gas coming from inside the dryer system.

A further problem resides in the presence of invading spurious CO gas from external sources, in particular coming from climate fluctuations, variations in ambient air or exhaust gases from cars, field burning of crops, human activity, etc., which causes the ambient CO gas, which enters into the system air, to vary greatly according to location and pollution in the plant, area, country and weather. Many decades larger CO gas content may thus be present in the inlet air and mask or overpower the CO gas generated from any smoldering powder inside the process. This problem is attempted solved for the prior art systems by using a reference ambient air sample and/or by calculating the difference between CO gas content in inlet(s)—and outlet(s) samples using a fixed reference CO gas value or a differential calculation, i.e. a subtraction of the summed CO gas contents from all inlets and the summed CO gas contents from all outlets.

SUMMARY OF THE INVENTION

With this background, it is therefore an object of the invention to provide a powder drying system adapted for early detection of smoldering nests by means of a carbon monoxide (CO) gas detection system, with which powder drying system the above mentioned problems and disadvantages are mitigated.

In a first aspect of the invention, these and further objects are obtained by a CO gas detection system adapted for detection of CO gas from smoldering powders in a powder drying system component, such as a spray dryer chamber, a fluid bed or a bag filter, which CO gas detection system comprises at least one inlet CO gas detector arranged on at least one gas inlet of a powder drying system component such as to provide at least one inlet CO gas content measurement, at least one outlet CO gas detector arranged on at least one gas outlet of a powder drying system component such as to provide at least one outlet CO gas content measurement, and an analyzing unit adapted for receiving the at least one inlet CO gas content measurement from the at least one inlet CO gas detector, receiving the at least one outlet CO gas content measurement from the at least one outlet CO gas detector and comparing the sum of the at least one inlet CO gas content measurement and the sum of the at least one outlet CO gas content measurement while compensating for dilution, mixing, and time delay of the outlet CO gas content measurement such as to provide a differential measurement, $\Delta C_{outlet}$, indicative of the CO gas content from smoldering powders in a powder drying system component, where at least the at least one outlet CO gas detector comprises an IR laser transmitter and is adapted for detecting over a measurement volume and is arranged on the at least one gas outlet in such a way that said measurement volume extends directly inside a gas flow in said at least one gas outlet.

Other components of a powder drying system to be surveyed could be cyclones, ducts and the like. It is even possible that the exterior of a powder drying system, i.e. the room in which the powder drying system or a component thereof is located, could be surveyed.

The CO gas detection system according to the invention thus employs as measurement principle absorption of an IR laser beam at a specific wavelength emitted and detected by the IR detector. For instance, the absorption spectrum of CO exhibits major peaks at around 2.3 µm and around 4.7 µm. The specific wavelength of the IR laser beam emitted and detected by the IR detector is therefore typically around 2.2 to 2.4 µm. The adsorption is proportional to the number of CO molecules in the gas, and therefore the concentration of CO gas in the gas can be calculated from the adsorption, pressure and temperature of the gas. Furthermore, as the absorption spectrum of methane ($CH_4$) exhibits a major peak at around 2.2 µm, the CO gas detection system may also be employed for detecting $CH_4$ gas.

By providing at least the at least one outlet CO gas detector as an IR-laser detector suitable for detecting over a measurement volume and arranging it on the gas outlet in such a way that its measurement volume extends directly inside a gas flow in the gas outlet, direct measurement of the CO gas concentration at the measurement site is obtained in real time. Thus, only the result of the measurement needs to be transferred to the analyzing unit, which may be done by simply transferring electronic or optical signals over a wired or, even better, wireless electronic or optical communication line. In other words, with the system according to the invention, no sample collection, sample preparation and sample transport is necessary. Consequently, there is no need for costly, time consuming, and complex sampling equipment and tubing system for transport of the gas samples to the analyzing unit. This in turn provides for a system comprising very few components and thus being cost efficient, and simple to install and retrofit. Also, the process flow in the spray dryer system parts is completely undisturbed by the measurement process, and the quality of the spray dried product is thus not influenced.

A further advantage lies in that the direct measurement of the CO gas concentration at the measurement site and digital, such as optical or electronic transfer of the result to the analyzing unit makes it possible to reduce the response time of the system, i.e. the time delay between individual measurements very considerably, and in practice to as low as about 1 second and can even be lower. This applies to all sizes of spray dryer systems, and is much lower than for the prior art systems.

Furthermore, with a system according to the invention only one initial calibration procedure is needed for commissioning of the CO gas detector and the calibration may be performed by injection of methane gas into the entire system, which is easier to acquire than the certified N2+CO gas. Therefore, the need for the specialists aside of the detector provider to perform calibration and handle the hazardous CO gas bottles for commissioning is eliminated. Thus, the system according to the invention is also both simple and cost efficient in maintenance, safer and easier to commission. The verification of the invention's measuring accuracy is only required once a year. If verification shows that the invention need adjustment/calibration, the $N_2$+CO (CO=8.0 ppm) gas mixture or methane is used for that.

By providing an analyzing unit adapted for comparing the inlet CO gas content measurement and the outlet CO gas content measurement to compensate for dilution, mixing, and time delay of the outlet CO gas content measurement such as to provide a differential measurement, $\Delta C_{outlet}$, indicative of the CO gas emanating from smoldering powders in a powder drying system component, it is made possible to take into account both spurious CO gas from external sources and dilution, mixing and time delay in the powder drying system into consideration in the analysis and thus the true CO gas content measurement. Thereby a CO gas detection system is provided with which the reliability and sensitivity when measuring on a small volume of gas is increased considerably, and the resulting CO gas measurement is very precise and highly reliable.

Indeed, experiments performed on a powder drying system with a CO gas detector system according to the invention has shown that the sensitivity of the system is sufficiently high to detect CO gas concentrations from smoldering nests of 1 ppm (parts per million) or below. For instance, it has been shown that for a large powder drying system CO gas concentrations of as low as 0.3 to 0.4 ppm may be detected, while as high a sensitivity as corresponding to detectability of CO gas concentrations of as low as 0.04 ppm has been proved. The sensitivity and precision of the measurements is crucial in order to have an early warning system. This is considerably lower than the prior art systems.

The lowered response time and the increased sensitivity in turn provides for an effective early warning enabling action to be taken at a very early point of time in case smoldering begins to take place.

In an embodiment the at least one inlet CO gas detector also comprises an IR laser transmitter and is adapted for detecting over a measurement volume and is provided on the at least one gas inlet in such a way that its measurement volume extends directly inside a gas flow in said gas inlet.

Thereby, a CO gas detection system is provided in which advantages similar to those described above are also achieved when obtaining the inlet CO gas measurement, and the sensitivity of the system is improved.

In an embodiment at least the at least one outlet CO gas detector and/or at least the at least one inlet CO gas detector comprises an IR laser transmitter and an IR receiver, and optionally a reflector the IR laser transmitter and the IR receiver being arranged on positions being one of mutually offset in a radial and/or longitudinal direction, mutually opposite and diametrically opposite such that its measurement volume extends between said positions.

In a further, optional, embodiment at least the at least one inlet CO gas detector and/or outlet CO gas detector comprises an IR laser transmitter and an IR receiver and at least one reflector, the IR laser transmitter and the IR receiver being arranged in the same position and the at least one reflector being arranged in a position being one of offset in a radial and/or longitudinal direction, mutually opposite and diametrically opposite with respect to the position of the IR laser transmitter and/or the IR receiver such that the measurement volume of the at least one inlet and/or outlet CO gas detector system extends between said positions.

By any of the two above mentioned embodiments a CO gas detection system being extremely simple in construction and very simple to mount, including retrofit on an existing powder drying system, is provided for. Such a CO gas detection system is also cost effective in both procurement and in maintenance. By using reflectors, the measurement volume can be increased, and thus improve the sensitivity of the system.

In an embodiment the measurement volume of the outlet CO gas detector and/or the measurement volume of the inlet CO gas detector extends over a length of at least 1 meter.

Thereby, a measurement volume is provided which is sufficiently large to obtain a CO gas content measurement being both highly representative of the CO gas concentration in the inlet or outlet and also enabling the required sensitivity. It is noted that the optimum length depends on the type and effect of the IR laser transmitter and/or IR receiver being used and may thus vary according thereto.

In an embodiment the measurement volume of the outlet CO gas detector and the measurement volume of the inlet CO gas detector may extend along any one of a radial direction of the gas inlet or gas outlet, along a longitudinal direction of the gas inlet or gas outlet perpendicular to the radial direction and a direction being inclined with respect to the longitudinal direction and/or the radial direction of the gas inlet or gas outlet.

Thereby, a CO gas detection system which is simple to mount on a powder drying system is obtained while simultaneously in a particularly simple manner ensuring that a measurement volume is provided which is sufficiently large to obtain a CO gas content measurement being both highly representative of the CO gas concentration in the inlet or outlet and also enabling the required sensitivity.

In an embodiment the at least one outlet CO gas detector and/or the at least one inlet CO gas detector further comprises at least one purging device arranged and adapted for purging the CO gas detector prior to providing the CO gas content measurement.

By providing a purging device, residues of powder originating from the spray drying process which could accumulate on the outlet CO gas detector and/or the inlet CO gas detector, particularly on IR receiver and the optical components placed in the duct, e.g. lenses, of the CO gas detector system, over time may be removed or such powder accumulation may even be avoided altogether. This in turn provides for the removal of noise and disturbances in the measurements originating from such powder accumulation, thus improving measurement quality even further.

Advantageously, the gas used by the purging device for purging the CO gas detector comprises no CO gas. Thus, at least a small part of the measurement range immediately in front of the CO gas detector in the system component in which the CO gas detector's measurement volume is to be positioned is kept free from retained CO, which could have an influence on the accuracy of measurement. Thereby, a well-defined start of the measurement volume containing the concentration of CO gas to be measured will be provided. If, on the other hand, CO gas is present in the gas used by the purging device for purging the CO gas detector, this CO gas will also be detected by the CO gas detector and thus add an unwanted contribution to the measurement.

In an embodiment at least the inlet CO gas detector and/or the outlet CO gas detector is cooled, preferably air cooled. Thereby, it becomes possible to avoid drift of the measured spectrum of the IR laser beam due to heating. It is noted that in embodiments where the outlet and/or inlet CO gas detector comprises a purging device, the purging device may simultaneously serve to air cool the CO gas detector.

In an embodiment the powder drying system further comprises a plurality of outlet CO gas detectors arranged on the same gas outlet and/or on outlets of different powder drying system components such as to provide a plurality of outlet CO gas content measurements, and/or a plurality of inlet CO gas detectors arranged on the same gas inlet and/or on inlets of different powder drying system components such as to provide a plurality of inlet CO gas content measurements.

Thereby, it becomes possible to detect CO gas concentrations originating from smoldering of powders at several sites simultaneously. This in turn provides for a further improved early warning while still keeping the system simple and cost effective in both structure, mounting and maintenance.

In an embodiment the analyzing unit is adapted for comparing the inlet CO gas content measurement and the outlet CO gas content measurement to obtain a differential measurement, $\Delta C_{outlet}(x)$, indicative of CO gas from smoldering powders in a powder drying system component at a given time x by means of the relation:

$$\Delta C_{outlet}(x) = C_{outlet,measured}(x) - C_{outlet}(x),$$

where:

$$C_{outlet}(x) = \frac{\left(\frac{C_{inlet}(x - t_p) * \text{FLOW}_{inlet}}{V_{spraydryer}}\right) * t_s + C_{outlet}(x - t_s)}{1 + \left(\frac{\text{FLOW}_{outlet} * t_s}{V_{spraydryer}}\right)},$$

and where:

$C_{outlet,measured}(x)$ is the concentration of CO gas in ppm in the gas outlet according to an outlet CO gas content measurement as measured by means of the outlet CO gas detector at the time x, $C_{outlet}(x)$ is the calculated concentration of CO gas in ppm in the gas outlet at the time x, $C_{outlet}(x-t_s)$ is the calculated concentration of CO gas in ppm in the gas outlet at the time x minus the sampling time $t_s$, i.e. the latest previously calculated value of the concentration of CO gas in ppm in the gas outlet, $C_{inlet}(x-t_p)$ is the concentration of CO gas in ppm in the gas inlet according to an inlet CO gas content measurement as measured by means of the inlet CO gas detector a number of seconds $t_p$ before the time x, $V_{spraydryer}$ is the volume of the spray dryer in $m^3$, $\text{FLOW}_{inlet}$ is the air flow in $m^3/s$ in the main air inlet, $\text{FLOW}_{outlet}$ is the total gas flow out of the spray dryer, calculated as the sum of the gas flow in each of the main gas outlet, the gas outlet of the static fluid bed and the gas outlet of the VIBRO-FLUIDIZER™ in $m^3/s$, and $t_s$ is the sampling time.

Thereby it becomes possible not only to take into account spurious CO gas from external sources and dilution, mixing and time delay in the powder drying system, but to do so continuously from production run to production run or measurement to measurement by dynamic modeling of the powder drying system, rather than—as in the prior art systems—using a fixed compensation value. Also, the above described model has proven particularly precise for all sizes of powder drying systems or plants and it is an advantage that flow and volume changes easily can be entered into the model, e.g. directly acquired from the PLC-system.

In an embodiment the inlet CO gas detector(s) and/or outlet CO gas detectors including, where provided, the purging device(s) may be mounted on inlet and/or outlet flanges welded to the inlet and/or outlet ducts. Thereby a simple, quick and durable mounting of the CO gas detectors is provided for.

Thereby the measurement range may be cleaned for components which may otherwise influence the CO gas content measurement negatively before the CO gas content measurement is carried out, e.g. by changing the length of the optical beam path through the inlet or outlet. This in turn provides for an improved measurement sensitivity.

According to the invention, the above and further objects are furthermore achieved by means of a method for detecting CO gas from smoldering powders in a powder drying system component, such as a spray dryer chamber, a fluid bed or a bag filter, of a powder drying system comprising a carbon monoxide (CO) gas detection system, the method comprising the steps of providing an inlet CO gas content measurement by means of an inlet CO gas detector arranged on an gas inlet of a powder drying system component, providing an outlet CO gas content measurement by means of at least one outlet CO gas detector arranged on an gas outlet of a powder drying system component, receiving the inlet CO gas content measurement from the inlet CO gas detector, receiving the outlet CO gas content measurement from the at least one outlet CO gas detector, comparing the inlet CO gas content measurement and the outlet CO gas content measurement to compensate for dilution, mixing, and time delay of the outlet CO gas content measurement such as to provide a differential measurement, $\Delta C_{outlet}$, indicative of CO gas from smoldering powders in a powder drying system component, where the at least one outlet CO gas detector comprises an IR laser transmitter and is adapted for detecting over a measurement volume and is, prior to providing the outlet CO gas content measurement, arranged on the gas outlet in such a way that its measurement volume extends directly inside a gas flow in the gas outlet.

Further features of a method according to the second aspect of the invention will be apparent from the below detailed description and are set forth in the dependent method claims.

BRIEF DESCRIPTION OF THE DRAWINGS

The invention will be described in more detail below by means of non-limiting examples of presently preferred embodiments and with reference to the schematic drawings, in which.

DETAILED DESCRIPTION OF EMBODIMENTS OF THE INVENTION

Figure 1:
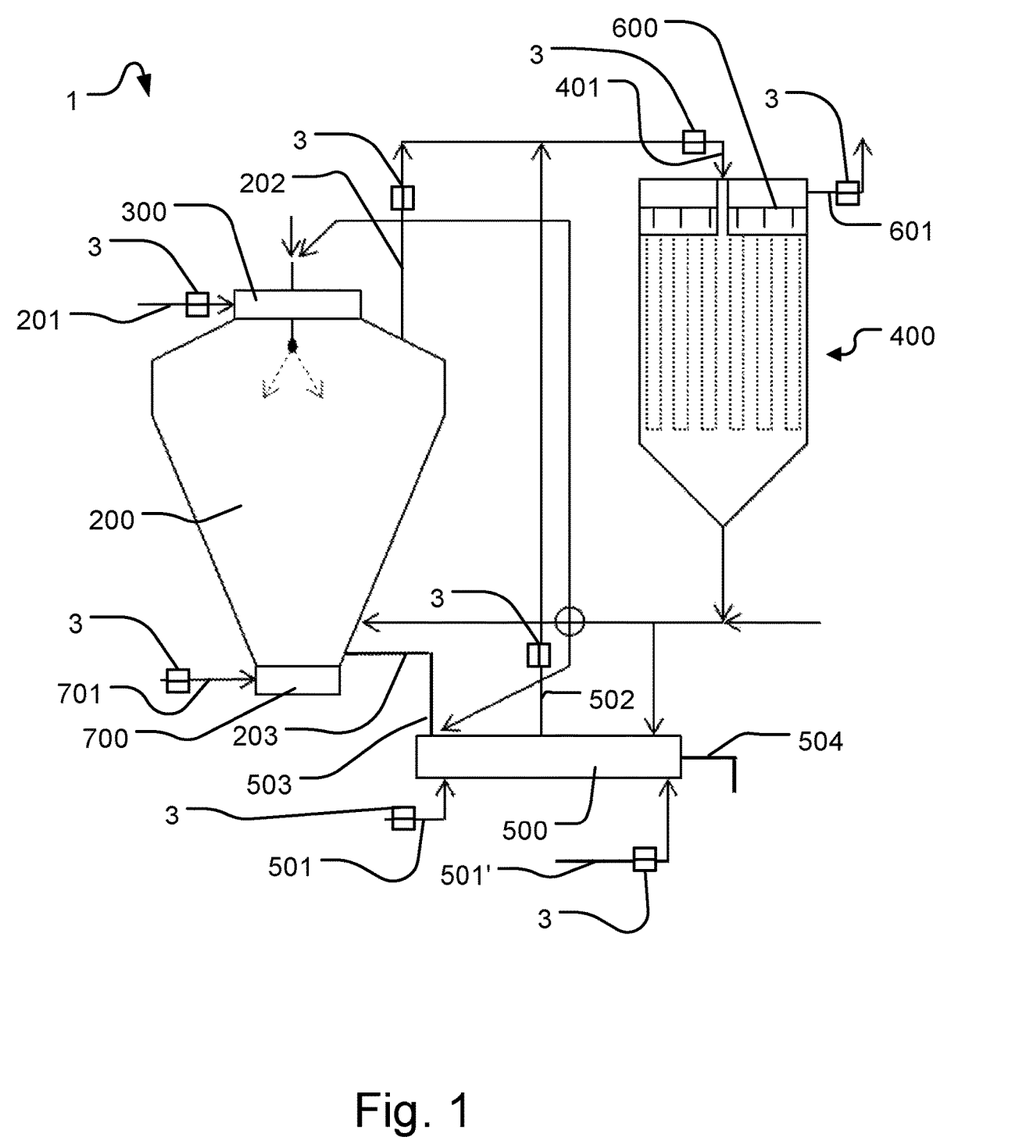
FIG. 1 shows a schematic view of the main components of a spray drying system in an embodiment of the first aspect of the invention, different exemplary positions of a CO gas detection system according to the invention being indicated.

FIG. 1 shows a schematic view of the main components of a powder drying system comprising a powder processing unit which by way of example in the embodiment shown is in the form of a spray drying system 1. In a manner known per se, the spray drying system 1 comprises a spray dryer with a drying chamber 200 and a process gas supply device 300, typically including an gas disperser. A gas inlet 201 is provided for intake of gas to the process gas supply device 300 and further to the drying chamber 200. At the lower end of the drying chamber 200, an outlet 203 for dried material is provided, and furthermore, for some types of powder drying systems, a further gas inlet 201' may be present. The drying chamber 200 also incorporates atomizing means, such as nozzles and/or a rotary atomizer wheel.

In the shown spray drying system 1, a static fluid bed 700 with air inlet 701 is provided and an after-treatment unit in the form of vibrating or static fluid bed 500 is provided. At one end, the vibrating or static fluid bed 500 comprises an inlet 503 at which it receives dried material from the outlet 203 of the drying chamber 200 for further treatment of the material, which is then to be collected at an outlet 504 at the other end of the vibrating or static fluid bed 500. The fluid bed 500 further comprises gas inlets 501 and 501' as well as a gas outlet 502. Further upstream or downstream equipment may be present as well.

Furthermore, the powder drying system comprises in addition to the spray drying system 1 a filter unit 400, to which spent process gas with particles entrained in the process gas is conducted. The filter unit 400 thus comprises a gas inlet 401 for spent process gas from one or more of the upstream operational units, a plurality of bag filters and a clean air outlet 601. The filter unit 400 may form part of a series of powder recovery units including further filter units and cyclones or bag filters, or any combination thereof. Furthermore, a cleaning arrangement 600 is shown in FIG. 1.

A number of conveying lines connect the operational units with each other in a manner known per se and will not be described in detail.

Figure 2:
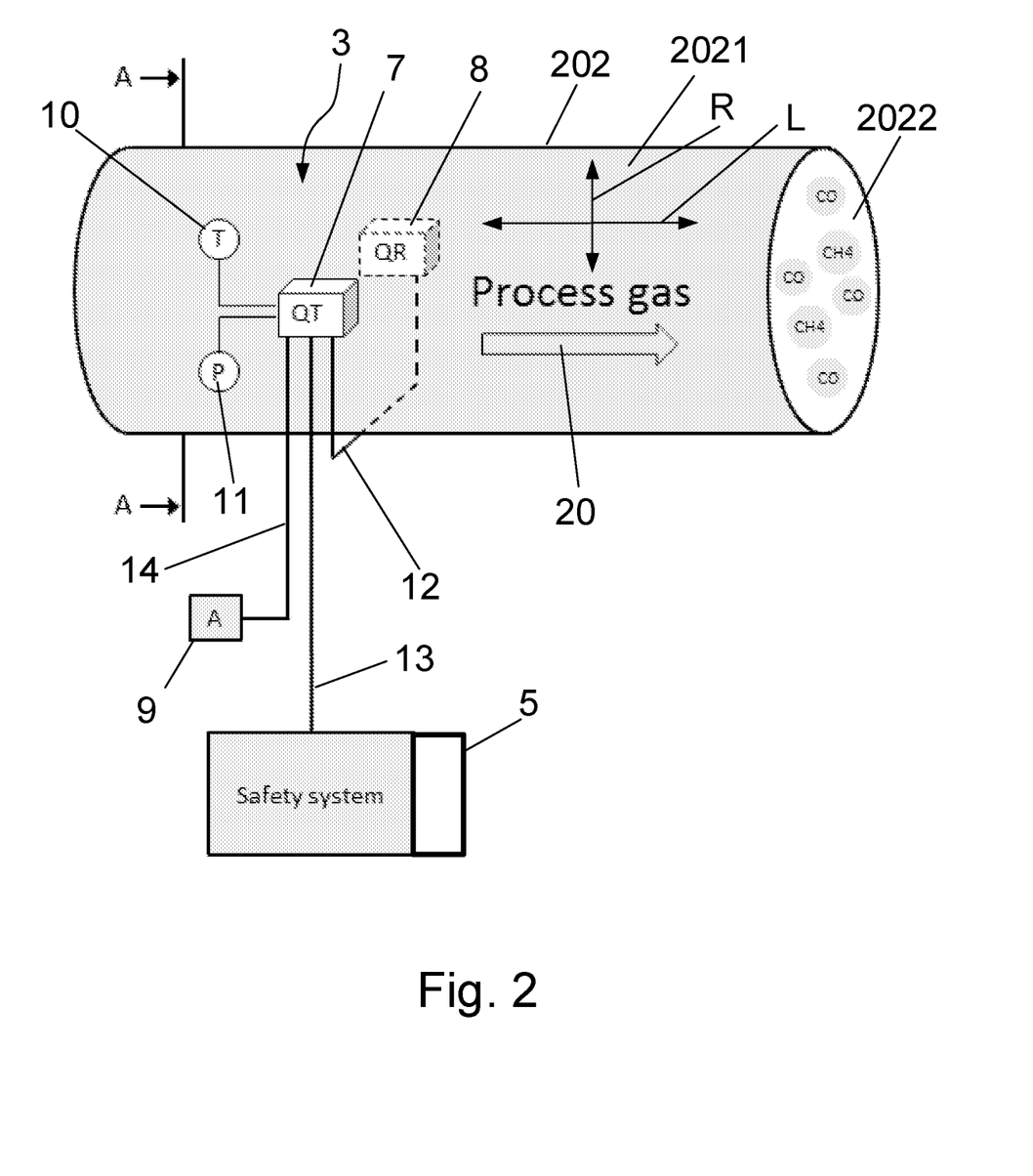
FIG. 2 shows a schematic view of a CO gas detection system in an embodiment of the invention, where the CO gas detection system is arranged on an outlet of the spray drying system.
Figure 3:
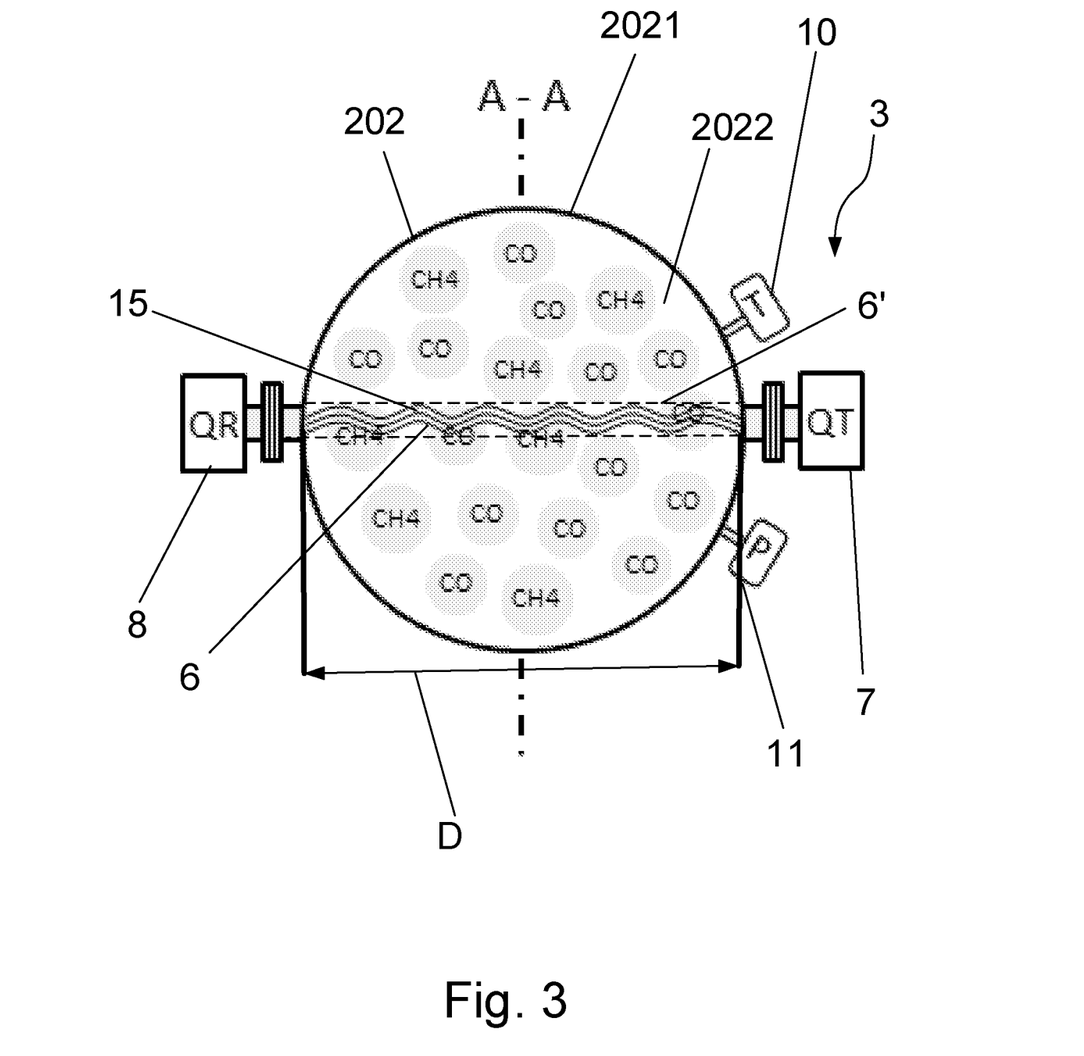
FIG. 3 shows a cross sectional view of a CO gas detection system according to FIG. 2.

The general configuration of the CO gas detection system of a spray drying system according to the invention will now be described in more detail with particular reference to FIGS. 2-3.

According to the invention the spray drying system 1 further comprises a carbon monoxide (CO) gas detection system adapted for detection of CO gas from smoldering powders in a spray drying system component, such as for instance the spray dryer chamber 200, the fluid bed 500 or the bag filter unit 400.

Generally, the CO gas detection system comprises at least one CO gas detector arranged on a gas outlet, herein denoted outlet CO gas detector, and at least one CO gas detector arranged on a gas inlet, herein denoted inlet CO gas detector. In FIG. 1 various exemplary and non-limiting possible positions of outlet CO gas detectors and inlet CO gas detectors are indicated. Since the at least one outlet CO gas detector and the at least one inlet CO gas detector is of identical or similar structure, both are indicated on FIG. 1 by the reference numeral 3, and FIGS. 2-3 illustrate an embodiment of a CO gas detector which by way of example is arranged on a gas outlet 202, but which may just as well have been arranged on a gas inlet.

Generally, the CO gas detection system comprises an outlet CO gas detector 3 arranged on an gas outlet, such as on an outer surface thereof, of a powder drying system component such as to provide an outlet CO gas content measurement. Referring to FIGS. 2 and 3, the CO gas detection system more particularly and by way of a non-limiting example comprises an outlet CO gas detector 3 arranged on the gas outlet 202 of the drying chamber 200 of the spray drying system 1. More particularly, the outlet CO gas detector 3 is arranged on an outer surface 2021 of the gas outlet 202 of the drying chamber 200. Generally, an outlet CO gas detector 3 may alternatively or additionally be arranged on a second or further gas outlet of the same or a second spray drying system component, such as those described above and/or such as indicated in FIG. 1.

The CO gas detection system may further comprise at least one inlet CO gas detector arranged on a gas inlet, such as on an outer surface thereof, of a powder drying system component such as to provide an inlet CO gas content measurement. The CO gas detection system more particularly and by way of a non-limiting example comprises an inlet CO gas detector arranged on the gas inlet 201 of the drying chamber 200 of the spray drying system 1. More particularly, the inlet CO gas detector is arranged on an outer surface of the gas inlet 201 of the drying chamber 200. Generally, one or more inlet CO gas detectors may, alternatively or additionally, be arranged on one or more gas inlets of other spray drying system components, such as those described above and/or such as indicated in FIG. 1. In a preferred embodiment, the inlet CO gas detector measuring IR radiation.

For instance, the outlet CO gas detector 3 and/or the inlet CO gas detector, respectively, may in some embodiments be mounted on flanges welded to the gas outlet and/or gas inlet, respectively.

The CO gas detection system further comprises an analyzing unit 5. The analyzing unit 5 is adapted for receiving the inlet CO gas content measurement from the inlet CO gas detector and for receiving the outlet CO gas content measurement from the at least one outlet CO gas detector 3. The analyzing unit 5 may thus comprise a receiver. The analyzing unit 5 is furthermore adapted for comparing the inlet CO gas content measurement and the outlet CO gas content measurement to compensate for dilution, mixing, and time delay of the outlet CO gas content measurement such as to provide a differential measurement, $\Delta C_{outlet}$, indicative of CO gas from smoldering powders in a spray drying system component, i.e. in the embodiment illustrated in the spray drying chamber 200. The analyzing unit 5 is thus electrically and/or optically connected to the inlet CO gas detector and the outlet CO gas detector 3 by means of a respective wired or wireless connection 13 (FIG. 2).

The analyzing unit 5 is furthermore adapted for, in case the result of the comparison shows an indication of CO gas from smoldering powders in a spray drying system component, taking an appropriate action. Such an appropriate action may comprise setting off an alarm, e.g. in the form of an acoustic or a visual signal, and/or automatically shutting down the spray drying system and/or activating fire-preventing means.

The analyzing unit 5 may thus, and as is shown on FIG. 2, form an integrated or stand-alone part of a safety system, which also comprises an alarm unit, e.g. in the form of an acoustic or a visual signaling unit. The alarm unit may alternatively be built into the analyzing unit 5. In any event, the analyzing unit is adapted for triggering the alarm unit and the alarm unit is adapted for emitting an alarm when the differential measurement, $\Delta C_{outlet}$, indicative of CO gas from smoldering powders in a spray drying system component is above a predetermined threshold value, typically being close to 0. Furthermore, the alarm unit may also be triggered if the analysis shows an erroneous function of the CO gas detection system, particularly to emit a signal dedicated to the purpose, which is a feature not being possible in the prior art system. The analyzing unit 5 is thus electrically and/or optically connected to the alarm unit by means of a wired or wireless connection.

Referring to FIGS. 2 and 3, the outlet CO gas detector 3 is an IR detector suitable for detecting over a measurement volume 6. The outlet CO gas detector 3 is arranged on the outlet 202 in such a way that its measurement volume 6 extends directly inside a (process) gas flow 20 in the outlet 202. More particularly, the outlet CO gas detector 3 comprises an IR laser transmitter 7 and an IR receiver 8. The IR laser transmitter 7 and the IR receiver 8 are arranged on opposite points, here but not mandatorily always on diametrically opposite points, on the outlet 202 such that its measurement volume 6, i.e. the volume through which the IR laser beam 15 of the IR detector extends when in operation and measuring, extends over a length D between the opposite points of the outlet 202 through the inside 2022 of the outlet 202. The IR laser transmitter 7 and the IR receiver 8 may furthermore be electrically and/or optically connected by means of a wired or wireless connection 12.

In alternative embodiments the outlet CO gas detector 3 may also comprise one or more IR reflectors, which reflectors may be arranged together with the IR laser transmitter, e.g. in the same housing, or apart from the emitter, e.g. in a different housing than the IR laser transmitter, such as in the housing of the IR receiver, or to redirect the laser light over one or more segments along one or more of the longitudinal direction, the radial direction and the cross sectional direction of the gas outlet. The same applies to the inlet CO gas detector.

The outlet CO gas detector 3 may further comprise at least one purging device 9 arranged and adapted for purging the outlet CO gas detector 3 prior to providing the outlet CO measurement. The purging device 9 is connected to the outlet CO gas detector 3, particularly to the IR laser transmitter 7 and to the outlet IR receiver 8, by means of an air tube 14.

The inlet CO gas detector may also be substantially identical to the outlet CO gas detector 3. The inlet CO gas detector may preferably comprise an IR laser transmitter and is adapted for detecting over a measurement volume. The inlet CO gas detector is then provided on the inlet 201 in such a way that its measurement volume extends directly inside a (process) gas flow in the inlet 201. More particularly, the inlet CO gas detector system comprises an IR laser transmitter and an IR receiver. The IR laser transmitter and the IR receiver are arranged on opposite points, possibly but not mandatorily diametrically opposite points, on the inlet 201 such that its measurement volume, i.e. the area in which the IR laser beam of the IR detector extends when in operation and measuring, extends over a length between the opposite points of the inlet 201 through the inside of the inlet 201. The IR laser transmitter and the IR receiver may furthermore be electrically and/or optically connected by means of a wired or wireless connection.

The inlet CO gas detector may further comprise at least one purging device arranged and adapted for purging the inlet CO gas detector prior to providing the inlet CO gas content measurement. The purging device is connected to the inlet CO gas detector, particularly to the IR laser transmitter and to the inlet IR receiver, by means of air tubes.

The measurement volume 6 of the outlet CO gas detector 3 and the measurement volume of the inlet CO gas detector may extend along any one of a radial direction R (FIG. 2) of the gas inlet or gas outlet as shown in FIG. 3, along a longitudinal direction L (FIG. 2) of the gas inlet or gas outlet perpendicular to the radial direction R and a direction being inclined with respect to both the longitudinal direction L and the radial direction R of the gas inlet or gas outlet. The measurement volume 6 of the outlet CO gas detector 3 and the measurement volume of the inlet CO gas detector may extend over a length of more than 1 meter, such as to provide for a measurement volume being sufficiently large to enable the desired sensitivity and precision of the measurements.

The measurement principle employed by the invention is thus adsorption of an IR laser beam at specific wavelengths emitted from the IR laser transmitter 7. The adsorption will be proportional to the number of molecules of CO in the process gas. Thus, from the adsorption as well as from the temperature and pressure of the process gas, the concentration of CO gas may be calculated based on analysis of the resulting adsorption spectrum, for instance in the manner described further below.

In a manner known per se to the skilled person within IR based CO gas content measurements, the outlet CO gas detector 3 may further comprise a first transmitter 10 for measuring process gas temperature for providing a process temperature compensation to the CO gas content measurement to compensate for the effects on the measurements caused by elevated temperatures caused by the IR laser beam, or in particular from elevated process temperatures compared to room temperature, which may otherwise shift the adsorption spectrum obtained. The outlet CO gas detector 3 may further comprise a second transmitter for 11 measuring process gas pressure for providing process pressure compensation to the calculation to compensate for the effects on the measurements caused by elevated process pressures compared to atmospheric pressure. Analogously, the inlet CO gas detector may further comprise a first transmitter for providing process temperature compensation and/or a second transmitter for providing process pressure compensation.

Furthermore, in some embodiments where the CO gas detection system comprises a purging device 9, the purging device 9 may also be arranged and adapted for purging a measurement range 6' (FIG. 3) inside the gas outlet before providing the outlet CO gas content measurement and/or be arranged and adapted for purging a part of a measurement range inside the gas inlet before providing the inlet CO gas content measurement.

Still further, the outlet CO gas detector 3 and/or the inlet CO gas detector, such as comprising the IR laser transmitter and or IR receiver, may in some embodiments be cooled, such as air cooled or even water cooled. For instance, the purging units may also serve as air cooling units. Alternatively, a separate cooling device may be provided.

Figure 4:
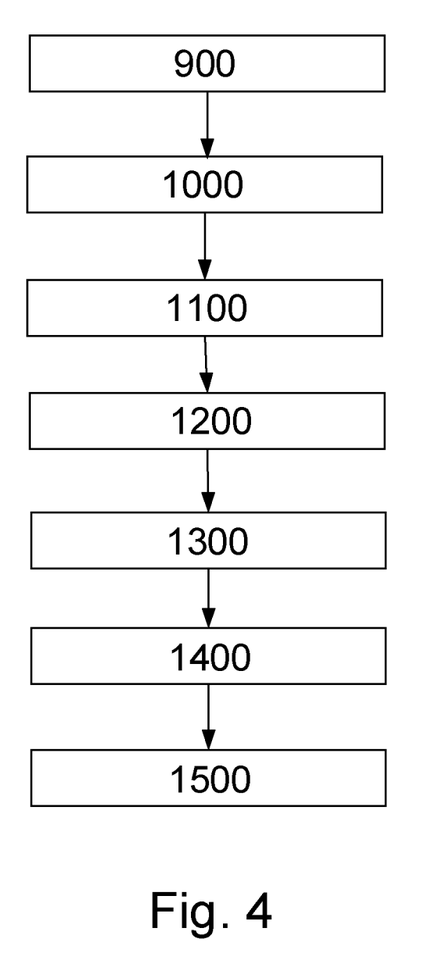
FIG. 4 illustrates schematically the steps of a method according to an embodiment of the invention.

Referring now to FIG. 4 exemplary embodiments of a method according to the invention will be described.

Prior to step 1000 a spray drying system with a CO gas detection system according to the invention is provided by mounting said CO gas detection system on the spray drying system. In step 1000, an inlet CO gas content measurement is provided by said at least one inlet CO gas detector. In step 1200 an outlet CO gas content measurement is provided by means of said at least one outlet CO gas detector. In step 1300 the inlet CO gas content measurement from the inlet CO gas detector is received by the analyzing unit 5. In step 1400 the outlet CO gas content measurement from the at least one outlet CO gas detector is received at the analyzing unit 5. In step 1500 the inlet CO gas content measurement and the outlet CO gas content measurement is compared by means of the analyzing unit 5 to compensate for dilution, mixing, and time delay of the outlet CO gas content measurement such as to provide a differential measurement, $\Delta C_{outlet}$, indicative of CO gas from smoldering powders in a spray drying system component. Finally, in step 1100, prior to the step 1200 of providing the outlet CO gas content measurement, the at least one outlet CO gas detector is provided as an outlet CO gas detector comprising an IR laser transmitter and being adapted for detecting over a measurement volume and is arranged on the gas outlet in such a way that its measurement volume extends directly inside a gas flow 20 in the inside 2022 of the gas outlet 202.

The method may furthermore comprise one or more of the following optional steps.

A step 900 of, prior to the step 1000 of providing the inlet CO gas content measurement, providing the inlet CO gas detector as an inlet CO gas detector optionally comprising an IR laser transmitter and being adapted for detecting over a measurement volume, and arranging the inlet CO gas detector on the gas inlet in such a way that its measurement volume extends directly inside a (process) gas flow in the inside of the gas inlet 201.

In embodiments where at least the outlet CO gas detector comprises an IR laser transmitter and an IR receiver, a step of arranging the IR laser transmitter and the IR receiver on opposite points, optionally diametrically opposite points, on the gas outlet 202, such as on an outer surface 2021 of the outlet 202, such that its measurement volume extends between the opposite points of the gas outlet 202.

In embodiments where the inlet CO gas detector comprises an IR laser transmitter and an IR receiver, a step of arranging the IR laser transmitter and the IR receiver on opposite points, optionally diametrically opposite points, on the gas inlet 201, such as on an outer surface of the inlet 201, such that its measurement volume extends between the opposite points of the gas inlet 201.

An optional step of purging the outlet CO gas detector prior to the step 1200 of providing the outlet CO gas content measurement.

An optional step of purging the inlet CO gas detector prior to the step 1300 of providing the inlet CO gas content measurement.

An optional step of cooling, preferably air cooling, the outlet CO gas detector and/or a step of cooling, preferably air cooling, the inlet CO gas detector.

An optional step of providing a plurality of outlet CO gas detectors, arranging the plurality of outlet CO gas detectors on the same gas outlet and/or on outlets of different spray drying system components, and a step of providing a plurality of outlet CO gas content measurements.

An optional step of providing a plurality of inlet CO gas detectors, arranging the plurality of inlet CO gas detectors on the same gas inlet and/or on inlets of different spray drying system components, and a step of providing a plurality of inlet CO gas content measurements.

An optional step of providing the outlet CO gas detector and/or the inlet CO gas detector with process temperature compensation and/or process pressure compensation prior to the step 1200 of providing the outlet CO gas content measurement and/or prior to the step 1000 of providing the inlet CO gas content measurement.

In the following the mathematical model lying behind the comparison performed by the analyzing unit 5 and forming part of the method performed by the powder drying system according to the invention, and more particularly forming part of the step of comparing of the method according to the invention will be described.

A rise in the CO gas concentration in the inlet air, $C_{inlet}$, will over time result in an elevated CO gas concentration in the outlet air, $C_{outlet}$. By mathematically modelling the spray drying system as a perfectly mixed tank plus a plug flow, $t_p$, i.e. a time delay, it becomes possible to calculate the CO gas concentration in the outlet air based on the CO gas concentration in the inlet air. The calculated CO gas concentration in the outlet air, $C_{outlet}$, is indicative of the naturally occurring fluctuations of the CO gas concentration in reaction to which the alarm system should not set off. Rather, the alarm system should only be set off in reaction to a rise in CO gas concentration originating from smoldering of powders in the spray drying system. The rise in CO gas concentration, or differential measurement, $\Delta C_{outlet}$, originating from smoldering may be expressed as:

$$\Delta C_{outlet} = C_{outlet,measured} - C_{outlet} \quad (1)$$

where $C_{outlet,\,measured}$ is the CO gas concentration in the outlet according to an outlet CO gas content measurement measured by the outlet CO gas detector.

To calculate $C_{outlet}$ the following model may be set up. First of all, the amount of CO gas accumulated per time unit in the spray drying system may be expressed as:

$$C_{inlet}*\text{FLOW}_{inlet} - C_{outlet}*\text{FLOW}_{outlet} \quad (2),$$

and as $$\frac{dC_{spray\,dryer}}{dt} * V_{spray\,dryer}. \quad (3)$$

In the above equations $\text{FLOW}_{inlet}$ is the air flow in m³/s in the main air inlet 201, $\text{FLOW}_{outlet}$ is the total gas flow in m³/s out of the spray drying system and $V_{spraydryer}$ is the volume of the spray drying system in m³.

The air flow in m³/s in the main air inlet 201, $\text{FLOW}_{inlet}$, is assumed to be constant over time, is equal to the flow in the main air inlet in the case that the static fluid bed and the VIBRO-FLUIDIZER™ have air inlets separate from the main air inlet, and is equal to the sum of the flow in each of the main air inlet, the air inlet of the static fluid bed and the air inlet of the VIBRO-FLUIDIZER™ if a common air inlet is used.

The total gas flow out of the spray drying system, $\text{FLOW}_{outlet}$, is calculated as the sum of the gas flow in each of the main gas outlet, the gas outlet of the static fluid bed and the gas outlet of the VIBRO-FLUIDIZER™ in m³/s.

The volume of the spray dryer in m³, $V_{spraydryer}$, may be determined experimentally by introducing CO gas into the spray dryer. A theoretical value may be obtained as $t_p*\text{FLOW}_{inlet}$, where $t_p$ is an assumed time delay of the gas flow through the spray drying system, i.e. the time it is assumed the gas flow takes to flow from the inlet CO gas detector through the spray dryer to the outlet CO gas detector.

Due to the assumed perfect mixing in the spray dryer, the CO gas concentration in the outlet air is equal to the CO gas concentration in the spray drying system ($dC_{spray\,dryer}/dt = dC_{outlet}/dt$). Due to the assumed time delay, $t_p$, of the gas flow through the spray drying system, the inlet CO gas concentration measured by the inlet CO gas detector at the time $t_p$ before a given point of time, x, is used for calculating the outlet CO gas concentration of the spray drying system at the time x:

$$\frac{dC_{outlet}(x)}{dt} = \frac{C_{inlet}(x-t_p)*\text{FLOW}_{inlet} - C_{outlet}(x)*\text{FLOW}_{outlet}}{V_{spray\,dryer}}, \quad (4)$$

where $C_{inlet}(x-t_p)$ is the concentration of CO gas in ppm measured by the inlet CO gas detector in the inlet at a number of seconds $t_p$ before the time x.

Using sampling steps of a small size, $t_s$, one obtains based on equation (4) above:

$$\frac{C_{outlet}(x) - C_{outlet}(x-t_s)}{t_s} = \frac{C_{inlet}(x-t_p)*\text{FLOW}_{inlet} - C_{outlet}(x)*\text{FLOW}_{outlet}}{V_{spray\,dryer}}, \quad (5)$$

Thus, by rearranging equation (5), the following relation for the calculated CO gas concentration in ppm in the outlet air, $C_{outlet}$, at a time x is arrived at:

$$C_{outlet}(x) = \frac{\left(\frac{C_{inlet}(x-t_p)*\text{FLOW}_{inlet}}{V_{spraydryer}}\right)*t_s + C_{outlet}(x-t_s)}{1 + \left(\frac{\text{FLOW}_{outlet}*t_s}{V_{spraydryer}}\right)}, \quad (6)$$

where $C_{outlet}(x-t_s)$ is the concentration of CO gas in ppm at the time x minus $t_s$—the sampling time—i.e. the latest previously calculated value of $C_{outlet}$.

Equation (6) may thus be used for comparing the inlet CO gas content measurement and the outlet CO gas content measurement. The result may then be inserted into equation (1) together with the outlet CO gas content measurement, $C_{outlet,\,measured}(x)$, obtained by the outlet CO gas detector at the time x to calculate the differential measurement, $\Delta C_{outlet}(x)$, indicative of the rise in CO gas concentration originating from smoldering at the time x, thus achieving:

$$\Delta C_{outlet}(x) = C_{outlet,\,measured}(x) - C_{outlet}(x) \quad (7).$$

Based on the thus calculated differential measurement, $\Delta C_{outlet}$, indicative of the rise in CO gas concentration originating from smoldering it may, for each calculation made, be determined whether an alarm should be set off and/or other suitable action be taken.

It should be noted that the above description of preferred embodiments serves only as an example, and that a person skilled in the art will know that numerous variations are possible without deviating from the scope of the claims.

For instance, and optionally, as methane ($CH_4$) has adsorption wavelengths being similar to those of CO, the method and/or device according to the invention may also be employed to detect $CH_4$ gas in a gas inlet or gas outlet of a spray drying component. The results of such a $CH_4$ gas detection may also be used to take into account the effects caused by the $CH_4$ gas interfering with the CO gas measurements, at least in case reasonably large quantities of $CH_4$ gas are present.

The invention claimed is:

1. A powder drying system comprising a CO gas detection system adapted for detection of CO gas from smoldering powders in a powder drying system component of a spray dryer chamber, a fluid bed, or a bag filter, wherein the CO gas detection system comprises:

at least one inlet CO gas detector arranged on at least one gas inlet of the powder drying system component to provide at least one inlet CO gas content measurement;

at least one outlet CO gas detector arranged on at least one gas outlet of the powder drying system component to provide at least one outlet CO gas content measurement; and an analyzing unit adapted for receiving the at least one inlet CO gas content measurement from the at least one inlet CO gas detector, receiving the at least one outlet CO gas content measurement from the at least one outlet CO gas detector and comparing a sum of the at least one inlet CO gas content measurement and a sum of the at least one outlet CO gas content measurement while compensating for dilution, mixing, and time delay of the outlet CO gas content measurement to provide a differential measurement, $\Delta C_{outlet}$, indicative of the CO gas content from smoldering powders in the powder drying system component, wherein at least the at least one outlet CO gas detector comprises an IR laser transmitter and is adapted to detect over a measurement volume and is arranged on the at least one gas outlet in such a way that said measurement volume extends directly inside a gas flow in said at least one gas outlet.

2. A powder drying system according to claim 1, wherein the at least one inlet CO gas detector also comprises an IR laser transmitter and is adapted to detect over a measurement volume and is provided on the at least one gas inlet in such a way that its measurement volume extends directly inside a gas flow in said gas inlet.

3. A powder drying system according to claim 1, wherein at least one of the at least one outlet CO gas detector or at least the at least one inlet CO gas detector comprises an IR laser transmitter and an IR receiver, wherein the IR laser transmitter and the IR receiver are arranged mutually offset in a radial direction, mutually offset in a longitudinal direction, or mutually opposite and diametrically opposite, such that its measurement volume extends between the IR laser transmitter and the IR receiver.

4. A powder drying system according to claim 1, wherein at least one of the measurement volume of the outlet CO gas detector or the measurement volume of the inlet CO gas detector extends over a length of at least 1 meter.

5. A powder drying system according to claim 1, wherein at least one of the at least one outlet CO gas detector or the at least one inlet CO gas detector further comprises at least one purging device arranged and adapted to purge at least one of the outlet CO gas detector prior to providing the outlet CO gas content measurement or the inlet CO gas detector prior to providing the inlet CO gas content measurement.

6. A powder drying system according to claim 1, wherein the at least one of the measurement volume of the outlet CO gas detector or the measurement volume of the inlet CO gas detector may extend along any one of:

a radial direction of the gas inlet or gas outlet, a longitudinal direction of the gas inlet or gas outlet perpendicular to the radial direction, or a direction being inclined with respect to the longitudinal direction or the radial direction of the gas inlet or gas outlet.

7. A powder drying system according to claim 1, further comprising at least one of:

a plurality of outlet CO gas detectors arranged on the same gas outlet or on outlets of different components of said powder drying system to provide a plurality of outlet CO gas content measurements, or a plurality of inlet CO gas detectors arranged on the same gas inlet or on inlets of different components of said powder drying system to provide a plurality of inlet CO gas content measurements.

8. A powder drying system according to claim 1, wherein the analyzing unit is adapted to compare the inlet CO gas content measurement and the outlet CO gas content measurement to obtain a differential measurement, $\Delta C_{outlet}(x)$, indicative of the CO gas content from smoldering powders in the powder drying system at a given time x by means of the relation:

$$\Delta C_{outlet}(x) = C_{outlet,measured}(x) - C_{outlet}(x),$$

where:

$$C_{outlet}(x) = \frac{\left(\frac{C_{inlet}(x-t_p)*FLOW_{inlet}}{V_{spraydryer}}\right)*t_s + C_{outlet}(x-t_s)}{1+\left(\frac{FLOW_{outlet}*t_s}{V_{spraydryer}}\right)},$$

and where:

$C_{outlet,measured}(x)$ is a concentration of CO gas in ppm in the gas outlet according to an outlet CO gas content measurement as measured by means of the outlet CO gas detector at the time x, $C_{outlet}(x)$ is a calculated concentration of CO gas in ppm in the gas outlet at the time x, $C_{outlet}(x-t_s)$ is a calculated concentration of CO gas in ppm in the gas outlet at the time x minus a sampling time $t_s$, the latest previously calculated value of the concentration of CO gas in ppm in the gas outlet, $C_{inlet}(x-t_p)$ is a concentration of CO gas in ppm in the gas inlet according to an inlet CO gas content measurement as measured by means of the inlet CO gas detector a number of seconds $t_p$ before the time x, $V_{spraydryer}$ is a volume of the spray dryer in m³, $FLOW_{inlet}$ is a air flow in m³/s in a main air inlet, $FLOW_{outlet}$ is a total gas flow out of the spray dryer, calculated as the sum of the gas flow in each of a main gas outlet, the gas outlet of a static fluid bed and the gas outlet of a vibro-fluidizer in m³/s, and $t_s$ is the sampling time.

9. A powder drying system according to claim 1, wherein at least one of the at least one inlet CO gas detector or outlet CO gas detector comprises an IR laser transmitter, an IR receiver, and at least one reflector, wherein the IR laser transmitter and the IR receiver are arranged in the same position and the at least one reflector is arranged offset in a radial direction, offset in a longitudinal direction, or mutually opposite and diametrically opposite with respect to the position of at least one of the IR laser transmitter or the IR receiver such that the measurement volume of the at least one inlet CO gas detetcor or outlet CO gas detector extends between the IR laser transmitter and the IR receiver via the at least one reflector.

10. A method for detecting CO gas from smoldering powder in a powder drying system component of a spray dryer chamber, a fluid bed or a bag filter, of a powder drying system comprising a carbon monoxide (CO) gas detection system, the method comprising:

providing an inlet CO gas content measurement by means of an inlet CO gas detector arranged on a gas inlet of the powder drying system component, providing an outlet CO gas content measurement by means of at least one outlet CO gas detector arranged on a gas outlet of the powder drying system component, receiving the inlet CO gas content measurement from the inlet CO gas detector, receiving the outlet CO gas content measurement from the at least one outlet CO gas detector, comparing the inlet CO gas content measurement and the outlet CO gas content measurement to compensate for dilution, mixing, and time delay of the outlet CO gas content measurement to provide a differential measurement, $\Delta C_{outlet}$, indicative of the CO gas content from smoldering powders in the powder drying system component, wherein the at least one outlet CO gas detector comprises an IR laser transmitter and is adapted to detect over a measurement volume and is, prior to providing the outlet CO gas content measurement, arranged on the gas outlet in such a way that its measurement volume extends directly inside a gas flow in the gas outlet.

* * * * *